US007098016B2

(12) United States Patent
Raines et al.

(10) Patent No.: US 7,098,016 B2
(45) Date of Patent: Aug. 29, 2006

(54) RIBONUCLEASE ZYMOGEN DESIGN

(75) Inventors: Ronald T. Raines, Madison, WI (US); Parit Plainkum, Madison, WI (US); Stephen M. Fuchs, Madison, WI (US)

(73) Assignees: Wisconsin Alumni Research Foundation, Madison, WI (US); Mahidol University, Nakornpathom (TH)

( * ) Notice: Subject to any disclaimer, the term of this patent is extended or adjusted under 35 U.S.C. 154(b) by 111 days.

(21) Appl. No.: 10/461,713

(22) Filed: Jun. 13, 2003

(65) Prior Publication Data

US 2004/0063116 A1 Apr. 1, 2004

Related U.S. Application Data

(60) Provisional application No. 60/389,238, filed on Jun. 14, 2002.

(51) Int. Cl.
*C12N 9/22* (2006.01)

(52) U.S. Cl. .................................................... 435/199

(58) Field of Classification Search ................. 435/199
See application file for complete search history.

(56) References Cited

U.S. PATENT DOCUMENTS 5,840,296 A * 11/1998 Raines et al. .............. 424/94.6
6,280,991 B1 * 8/2001 Raines ....................... 435/199

FOREIGN PATENT DOCUMENTS

WO WO 99/47640 * 9/1999
WO WO 00/62605 10/2000

OTHER PUBLICATIONS

Plainkum, P. et al. (2001) Abstracts Of Papers, 222nd ACS National Meeting, Chicago, IL, Aug. 26, 2001-Aug. 30, 2001, Abst. No. 92.*
Klink, et al. (2000) J. Biol. Chem. 275 (23), 17463-17467.*
Fleming, I., et al., "Phosphorylation of Thr495 Regulates Ca2+/ Calmodulin-Dependent Endothelial Nitric oxide Synthase Activity," Circulation Research Jun. 8, 2001.
Lee, C. M., et al., "Oligomerization of Endothelial Nitric Oxide Synthase," The Journal of Biological Chemistry 270:27403-27406 (1995).
Robinson, L.J., et al., "Mutagenesis of palmitoylation sites in endothelial nitric oxide synthase identifies a novel motif . . . ," Proc. Natl. Acad. Sci. USA 92:11776-11780 (1995).
Zhang, J.L., et al., "Reductase Domain Cysteines 1048 and 1114 Are Critical . . . ," Biochemical and Biophysical Research Communications 226:293-300 (1996).

* cited by examiner

*Primary Examiner*—Charles L. Patterson, Jr.
(74) *Attorney, Agent, or Firm*—Quarles & Brady LLP

(57) ABSTRACT

An enzyme is re-engineered to be a zymogen, an enzyme precursor which is converted into an enzyme by protease cleavage. In the example described here, an RNase A enzyme is converted into a zymogen by adding to the enzyme a bridge of amino acids linking the amino and carboxyl termini of the enzyme. The bridge has built in it a protease cleavage site for a specific protease, for example the protease plasmepsin II, produced by the malaria parasite. Since RNase A can be made cytotoxic, this permits a cytotoxic enzyme to be made in the form of a zymogen that becomes active only when it is acted on by a protease only present in a particular target cell such as a pathogen.

16 Claims, 4 Drawing Sheets

(SEQ ID NO:49).

SEQUENCE LISTING

```
<160> NUMBER OF SEQ ID NOS: 58

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:
      oligonucleotide

<400> SEQUENCE: 1

Lys Pro Ile Glu Phe
  1             5


<210> SEQ ID NO 2
<211> LENGTH: 4
<212> TYPE: PRT
<213> ORGANISM: Artificial Sequence
```

-continued

<220> FEATURE:
<223> OTHER INFORMATION: Description of Artificial Sequence:
      oligonucleotide

<400> SEQUENCE: 2

Leu Glu Leu Lys
  1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence:
      oligonucleotide

<400> SEQUENCE: 3

Thr Ala Thr Ile Met
  1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:
      oligonucleotide

<400> SEQUENCE: 4

Met Gln Arg Gly Asn
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:
      oligonucleotide

<400> SEQUENCE: 5

Glu Asp Val Val Cys Cys
  1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:
      oligonucleotide

<400> SEQUENCE: 6

Ser Met Ser Tyr Lys
  1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:
      oligonucleotide

<400> SEQUENCE: 7

Val Ser Arg Thr Leu Gln
  1               5

-continued

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:
oligonucleotide

<400> SEQUENCE: 8

Ser Gly Phe Lys
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:
oligonucleotide

<400> SEQUENCE: 9

Gly Pro Leu Gly
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:
oligonucleotide

<400> SEQUENCE: 10

Met Leu Ser His
1

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:
oligonucleotide

<400> SEQUENCE: 11

Lys Gly Pro Pro Val Ile Leu
1 5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:
oligonucleotide

<400> SEQUENCE: 12

Pro Ile Gln Ala Pro
1 5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:
oligonucleotide -continued

```
<400> SEQUENCE: 13

Lys Pro Ile Glu Phe Leu Glu Leu Lys
  1               5


<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence:
      oligonucleotide

<400> SEQUENCE: 14

Gly Ser Gly Lys Pro Ile Glu Phe Leu Glu Leu Lys Ala Gly
  1               5                   10


<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence:
      oligonucleotide

<400> SEQUENCE: 15

Gly Ser Lys Pro Ile Glu Phe Leu Glu Leu Lys Ala Gly
  1               5                   10


<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence:
      oligonucleotide

<400> SEQUENCE: 16

Gly Ser Gly Lys Pro Ile Glu Phe Leu Glu Leu Lys Gly Ala Gly
  1               5                   10                  15


<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17

cacaagtttc cttgccggcc gccggctggg cagcgag                             37


<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18

ccgcaagctt gtcgaggatc ccactgaagc atcaaa                              36


<210> SEQ ID NO 19
<211> LENGTH: 31
<212> TYPE: DNA
<213> ORGANISM: Artificial Sequence
<220> FEATURE:
```

-continued

<223> OTHER INFORMATION: Description of Artificial Sequence:
      oligonucleotide

<400> SEQUENCE: 19
gatctaaacc gattgaattt ctggaactga a 31

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
ggccttcagt tccagaaatt caatcggttt a 31

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
gatctggcaa accgattgaa tttctggaac tgaa 34

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
ggccttcagt tccagaaatt caatcggttt gcca 34

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
gatctggcaa accgattgaa tttctggaac tgggcaa 37

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
ggccttgccc agttccagaa attcaatcgg tttgcca 37

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence:

-continued oligonucleotide

<400> SEQUENCE: 25
aaggaaactg cagcagccaa gtttgagcgg cagc 34

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence:
oligonucleotide

<400> SEQUENCE: 26
gctgccgctc aaacttggct gctgcagttt cctt 34

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence:
oligonucleotide

<400> SEQUENCE: 27
gcatcaaagt ggactggcac gtacgggttt ccc 33

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence:
oligonucleotide

<400> SEQUENCE: 28
gggaaacccg tacgtgccag tccactttga tgc 33

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence:
oligonucleotide

<400> SEQUENCE: 29
cgtgagcata tgtgttccaa gtacccc 27

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence:
oligonucleotide

<400> SEQUENCE: 30
gttggggtcg acctactagc acgtctcacg gcagtc 36

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence:
oligonucleotide -continued

<400> SEQUENCE: 31
gttgacccgc atatgagcag ctccaactac tgtaaccaga tgatg 45

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence:
oligonucleotide

<400> SEQUENCE: 32
cgataaggcg tcgactacta ggcagcggaa gtgct 35

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence:
oligonucleotide

<400> SEQUENCE: 33
ggccatatgc tgaccaaaga tcgatgcaag 30

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence:
oligonucleotide

<400> SEQUENCE: 34
cacgtcgacc tactagttcc ggctcttcat catc 34

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence:
oligonucleotide

<400> SEQUENCE: 35
ggccatatgt ccctggctga tgtccaggcc 30

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence:
oligonucleotide

<400> SEQUENCE: 36
cacgtcgacc tactactcgt gcacaaaggt gttc 34

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence:
oligonucleotide -continued

<400> SEQUENCE: 37
ggccatatga aaaatgttgc ctgcaag 27

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence:
oligonucleotide

<400> SEQUENCE: 38
cacgtcgacc tactactggg agcacacggc ctg 33

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence:
oligonucleotide

<400> SEQUENCE: 39
ggccatatga attgctacca gagctactcc 30

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence:
oligonucleotide

<400> SEQUENCE: 40
gtgctcgagc tactaattct tgcaggcaac att 33

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence:
oligonucleotide

<400> SEQUENCE: 41
ggccatatgt ccaccatgag catcaccgac 30

<210> SEQ ID NO 42
<211> LENGTH: 34
<212> TYPE: DNA
<213> ORGANISM: Artificial Sequence
<220> FEATURE:
<223> OTHER INFORMATION: Description of Artificial Sequence:
oligonucleotide

<400> SEQUENCE: 42
cacgtcgacc tactagtagc tctggtagca attg 34

<210> SEQ ID NO 43
<211> LENGTH: 47
<212> TYPE: DNA
<213> ORGANISM: Artificial Sequence
<220> FEATURE:
<223> OTHER INFORMATION: Description of Artificial Sequence:
oligonucleotide

<400> SEQUENCE: 43

-continued caacgccttc atatgagctc caagtacccc aactgtgcct acaagac 47

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence:
oligonucleotide

<400> SEQUENCE: 44
ctgacggcag tcgactacta ccctgtctca cggcagtc 38

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence:
oligonucleotide

<400> SEQUENCE: 45
ggccatatgc acatcattgt ggcttgtgag 30

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence:
oligonucleotide

<400> SEQUENCE: 46
cacgtcgacc tactatttat tcgcctgggt ggtc 34

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence:
oligonucleotide

<400> SEQUENCE: 47
ggccatatgt acgtgccatg tcactttg 28

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence:
oligonucleotide

<400> SEQUENCE: 48
cacgtcgacc tactagtttc cctcacaagc cac 33

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence:short
polypeptide

<400> SEQUENCE: 49

-continued

```
Gly Ala Lys Leu Glu Leu Phe Glu Ile Pro Lys Gly Ser Gly
  1               5                  10


<210> SEQ ID NO 50
<211> LENGTH: 124
<212> TYPE: PRT
<213> ORGANISM: Bos taurus

<400> SEQUENCE: 50

Lys Glu Thr Ala Ala Ala Lys Phe Glu Arg Gln His Met Asp Ser Ser
  1               5                  10                  15

Thr Ser Ala Ala Ser Ser Ser Asn Tyr Cys Asn Gln Met Met Lys Ser
             20                  25                  30

Arg Asn Leu Thr Lys Asp Arg Cys Lys Pro Val Asn Thr Phe Val His
         35                  40                  45

Glu Ser Leu Ala Asp Val Gln Ala Val Cys Ser Gln Lys Asn Val Ala
     50                  55                  60

Cys Lys Asn Gly Gln Thr Asn Cys Tyr Gln Ser Tyr Ser Thr Met Ser
 65                  70                  75                  80

Ile Thr Asp Cys Arg Glu Thr Gly Ser Ser Lys Tyr Pro Asn Cys Ala
                 85                  90                  95

Tyr Lys Thr Thr Gln Ala Asn Lys His Ile Ile Val Ala Cys Glu Gly
            100                 105                 110

Asn Pro Tyr Val Pro Val His Phe Asp Ala Ser Val
        115                 120


<210> SEQ ID NO 51
<211> LENGTH: 124
<212> TYPE: PRT
<213> ORGANISM: Bos taurus

<400> SEQUENCE: 51

Lys Glu Ser Ala Ala Ala Lys Phe Glu Arg Gln His Met Asp Ser Gly
  1               5                  10                  15

Asn Ser Pro Ser Ser Ser Ser Asn Tyr Cys Asn Leu Met Met Cys Cys
             20                  25                  30

Arg Lys Met Thr Gln Gly Lys Cys Lys Pro Val Asn Thr Phe Val His
         35                  40                  45

Glu Ser Leu Ala Asp Val Lys Ala Val Cys Ser Gln Lys Lys Val Thr
     50                  55                  60

Cys Lys Asn Gly Gln Thr Asn Cys Tyr Gln Ser Lys Ser Thr Met Arg
 65                  70                  75                  80

Ile Thr Asp Cys Arg Glu Thr Gly Ser Ser Lys Tyr Pro Asn Cys Ala
                 85                  90                  95

Tyr Lys Thr Thr Gln Val Glu Lys His Ile Ile Val Ala Cys Gly Gly
            100                 105                 110

Lys Pro Ser Val Pro Val His Phe Asp Ala Ser Val
        115                 120


<210> SEQ ID NO 52
<211> LENGTH: 124
<212> TYPE: PRT
<213> ORGANISM: Mus musculus

<400> SEQUENCE: 52

Arg Glu Ser Ala Ala Gln Lys Phe Gln Arg Gln His Met Asp Pro Asp
  1               5                  10                  15

Gly Ser Ser Ile Asn Ser Pro Thr Tyr Cys Asn Gln Met Met Lys Arg
```

-continued

```
            20                  25                  30

Arg Asp Met Thr Asn Gly Ser Cys Lys Pro Val Asn Thr Phe Val His
        35                  40                  45

Glu Pro Leu Ala Asp Val Gln Ala Val Cys Ser Gln Glu Asn Val Thr
    50                  55                  60

Cys Lys Asn Arg Lys Ser Asn Cys Tyr Lys Ser Ser Ser Ala Leu His
65                  70                  75                  80

Ile Thr Asp Cys His Leu Lys Gly Asn Ser Lys Tyr Pro Asn Cys Asp
                85                  90                  95

Tyr Lys Thr Thr Gln Tyr Gln Lys His Ile Ile Val Ala Cys Glu Gly
            100                 105                 110

Met Pro Tyr Val Pro Val His Phe Asp Ala Thr Val
        115                 120


<210> SEQ ID NO 53
<211> LENGTH: 104
<212> TYPE: PRT
<213> ORGANISM: Rana pipiens

<400> SEQUENCE: 53

Gln Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Met Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys
            100


<210> SEQ ID NO 54
<211> LENGTH: 128
<212> TYPE: PRT
<213> ORGANISM: Homo sapiens

<400> SEQUENCE: 54

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30

Arg Asn Met Thr Gln Gly Arg Cys Lys Pro Val Asn Thr Phe Val His
        35                  40                  45

Glu Pro Leu Val Asp Val Gln Met Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
```

-continued

```
        115                 120                 125

<210> SEQ ID NO 55
<211> LENGTH: 134
<212> TYPE: PRT
<213> ORGANISM: Homo sapiens

<400> SEQUENCE: 55

Lys Pro Pro Gln Phe Thr Trp Ala Gln Trp Phe Glu Thr Gln His Ile
  1               5                  10                  15

Asn Met Thr Ser Gln Gln Cys Thr Asn Ala Met Gln Val Ile Asn Asn
             20                  25                  30

Tyr Gln Arg Arg Cys Lys Asn Gln Asn Thr Phe Leu Leu Thr Thr Phe
         35                  40                  45

Ala Asn Val Val Asn Val Cys Gly Asn Pro Asn Met Thr Cys Pro Ser
     50                  55                  60

Asn Lys Thr Arg Lys Asn Cys His His Ser Gly Ser Gln Val Pro Leu
 65                  70                  75                  80

Ile His Cys Asn Leu Thr Thr Pro Ser Pro Gln Asn Ile Ser Asn Cys
                 85                  90                  95

Arg Tyr Ala Gln Thr Pro Ala Asn Met Phe Tyr Ile Val Ala Cys Asp
            100                 105                 110

Asn Arg Asp Gln Arg Arg Asp Pro Pro Gln Tyr Pro Val Val Pro Val
        115                 120                 125

His Leu Asp Arg Ile Ile
    130

<210> SEQ ID NO 56
<211> LENGTH: 133
<212> TYPE: PRT
<213> ORGANISM: Homo sapiens

<400> SEQUENCE: 56

Arg Pro Pro Gln Phe Thr Arg Ala Gln Trp Phe Ala Ile Gln His Ile
  1               5                  10                  15

Ser Leu Met Pro Pro Arg Cys Thr Ile Ala Met Arg Ala Ile Asn Asn
             20                  25                  30

Tyr Arg Trp Arg Cys Lys Asn Gln Asn Thr Phe Leu Arg Thr Thr Phe
         35                  40                  45

Ala Asn Val Val Asn Val Cys Gly Asn Gln Ser Ile Arg Cys Pro His
     50                  55                  60

Asn Arg Thr Leu Asn Asn Cys His Arg Ser Arg Phe Arg Val Pro Leu
 65                  70                  75                  80

Leu His Cys Asp Leu Ile Asn Pro Gly Ala Gln Asn Ile Ser Asn Cys
                 85                  90                  95

Arg Tyr Ala Asp Arg Pro Gly Arg Arg Phe Tyr Val Val Ala Cys Asp
            100                 105                 110

Asn Arg Asp Pro Arg Asp Ser Pro Arg Tyr Pro Val Val Pro Val His
        115                 120                 125

Leu Asp Thr Thr Ile
    130

<210> SEQ ID NO 57
<211> LENGTH: 119
<212> TYPE: PRT
<213> ORGANISM: Homo sapiens

<400> SEQUENCE: 57
```

-continued

```
Gln Asp Gly Met Tyr Gln Arg Phe Leu Arg Gln His Val His Pro Glu
  1               5                  10                  15

Glu Thr Gly Gly Ser Asp Arg Tyr Cys Asp Leu Met Met Gln Arg Arg
             20                  25                  30

Lys Met Thr Leu Tyr His Cys Lys Arg Phe Asn Thr Phe Ile His Glu
         35                  40                  45

Asp Arg Trp Asn Ile Arg Ser Ile Cys Ser Thr Thr Asn Ile Gln Cys
     50                  55                  60

Lys Asn Gly Lys Met Asn Cys His Glu Gly Val Val Lys Val Thr Asp
 65                  70                  75                  80

Cys Arg Asp Thr Gly Ser Ser Arg Ala Pro Asn Cys Arg Tyr Arg Ala
                 85                  90                  95

Ile Ala Ser Thr Arg Arg Val Val Ile Ala Cys Glu Gly Asn Pro Gln
            100                 105                 110

Val Pro Val His Phe Asp Gly
        115


<210> SEQ ID NO 58
<211> LENGTH: 123
<212> TYPE: PRT
<213> ORGANISM: Homo sapiens

<400> SEQUENCE: 58

Gln Asp Asn Ser Arg Tyr Thr His Phe Leu Thr Gln His Tyr Asp Ala
  1               5                  10                  15

Lys Pro Gln Gly Arg Asp Asp Arg Tyr Cys Glu Ser Ile Met Arg Arg
             20                  25                  30

Arg Gly Leu Thr Ser Pro Cys Lys Asx Ile Asn Thr Phe Ile His Gly
         35                  40                  45

Asn Lys Arg Ser Ile Lys Ala Ile Cys Glu Asn Lys Asn Gly Asn Pro
     50                  55                  60

His Arg Glu Asn Leu Arg Ile Ser Lys Ser Ser Phe Gln Val Thr Thr
 65                  70                  75                  80

Cys Lys Leu His Gly Gly Ser Pro Trp Pro Pro Cys Gln Tyr Arg Ala
                 85                  90                  95

Thr Ala Gly Phe Arg Asn Val Val Val Ala Cys Glu Asn Gly Leu Pro
            100                 105                 110

Val His Leu Asp Gln Ser Ile Phe Arg Arg Pro
        115                 120
```

RIBONUCLEASE ZYMOGEN DESIGN

CROSS-REFERENCE TO RELATED APPLICATIONS

This application claims priority from U.S. provisional patent application No. 60/389,238 filed Jun. 14, 2002.

STATEMENT REGARDING FEDERALLY SPONSORED RESEARCH OR DEVELOPMENT

To be determined.

BACKGROUND OF THE INVENTION

The simplest definition of enzymes is that enzymes are proteins which can act as catalysts for a chemical reaction. As with all proteins, the amino acid sequence and the three-dimensional structure of enzymes are both important to the proper biological functioning of enzymes. Some enzymes are not functional as enzymes in the normal form in which they are synthesized originally in living cells. Instead, these enzymes are expressed as an enzyme precursor known as a zymogen. A zymogen is acted on by some other enzymatic process in or out of the cell to convert the zymogen into the enzymatically active form of the protein. Typically enzymes which could cause damage to cellular biochemical processes, like proteases, are produced as zymogens, thus permitting their activity to be controlled more precisely. Zymogens are inactive as expressed, and thus can be stored or transported safely and then activated by proteolytic activity only when needed.

In living cells, biological polymers such as proteins and nucleic acids must continually be digested into their monomers which can then be recycled for use in making new proteins or nucleic acids. Proteases digest proteins and nucleases digest nucleic acids. Among the best studied of nucleases are the ribonucleases which are adapted to digesting RNA molecules. In particular, the sequence, the three-dimensional structure, and many aspects of the functioning of ribonuclease A (RNase A) have been characterized, particularly with regard to bovine pancreatic ribonuclease A. RNase A exists in cells in balance with a ribonuclease inhibitor (RI), which binds to RNase A to inhibit its activity. It has already been found that adding a moiety to RNase A that acts to provide a steric barrier to binding between RI and RNase A causes the RNase to be uncontrolled by the RI and therefore cytotoxic, presumably by digesting needed RNA species in the cell.

It is a characteristic of proteases that they have specific amino acid sequences in target proteins that they recognize to digest a specific peptide bond. Many types of cells or organisms have specific proteases that recognize specific amino acid sequences for their target cleavage site. It is thus possible to design proteins which will be enzymatically cleaved only by proteases present in a select group, type or species of target cells.

Other objects, features and advantages of the invention will become apparent upon consideration of the following detailed description.

DETAILED DESCRIPTION OF THE INVENTION

Figure 1:
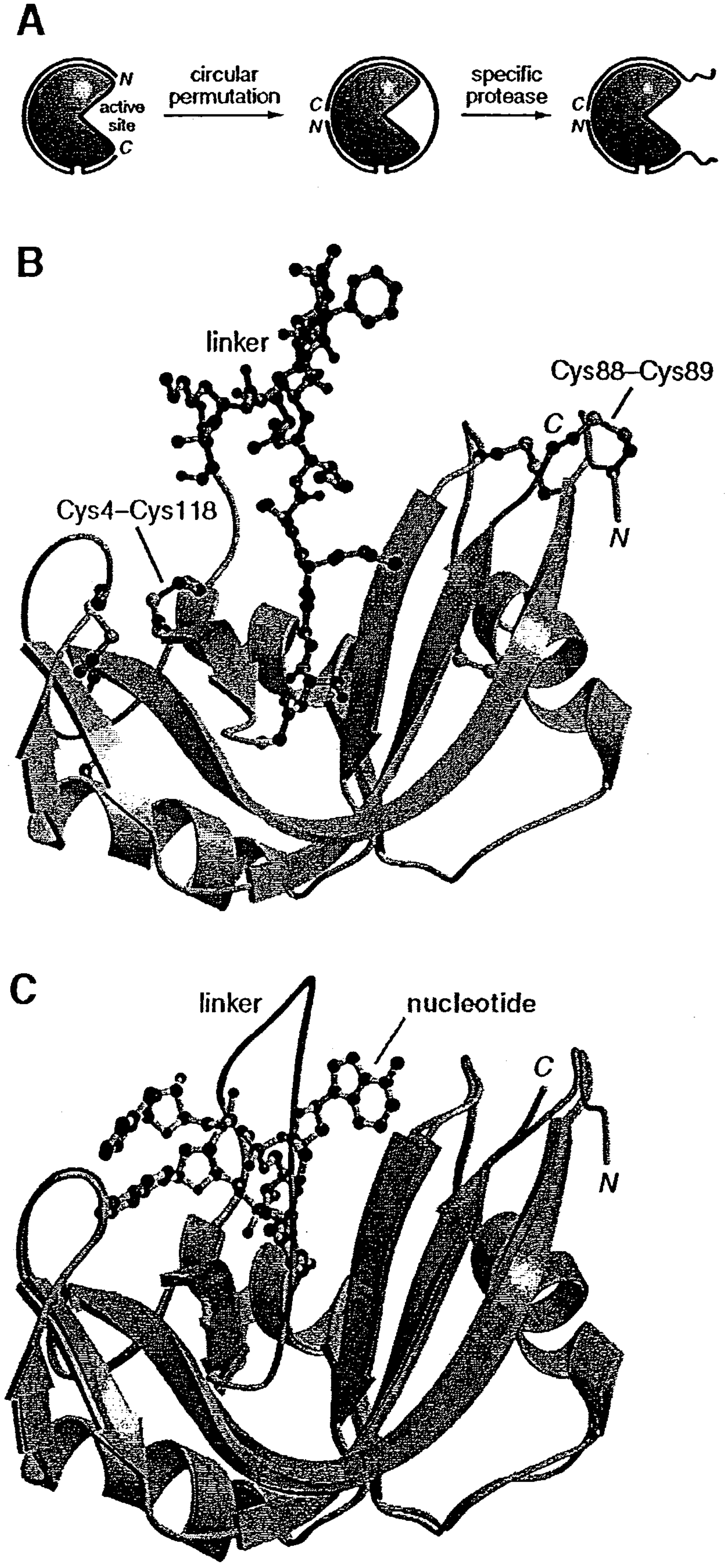
FIG. 1 is an illustration of the three dimensional structure of the RNase A protein.

It is revealed here that it is possible to design novel zymogens that will become enzymatically active only when acted upon by a specific protease. It is also taught here that protein re-engineering can include altering the start site and end terminus of native enzymes without necessarily making the enzymes inactive. Based on these teachings, it is now possible to design specific zymogens to be active only in targeted locations or cells, while still retaining the ability to perform proper biological activity.

What is described here is a new option for the control of enzymatic activity of ribonucleases specifically, and other enzymes in general. This option is the creation of a zymogen which will become enzymatically active only when the zymogen is activated by a particular protease. By selecting a protease which occurs only in a pathogen, or in cells infected by a pathogen, or in cells with a particular disease state, it is possible to construct the zymogen so that the enzymatic activity only occurs when the zymogen encounters a pathogenic cell or a diseased cell. It is already known how to convert RNase A to a cytotoxic form, as taught in the specification of U.S. Pat. No. 5,840,296 and No. 6,280,991, the disclosure of which is hereby incorporated by reference. The combination of these two techniques of protein engineering make it possible to design a zymogen which will be converted into a cytotoxic enzyme when, and only when, the zymogen encounters an enzyme from a pathogen or a cell in a particular diseased state, which can convert the zymogen into active enzyme.

In the specific embodiment of the technology disclosed here, a ribonuclease zymogen has been designed, this being the first known example of a zymogen of a ribonuclease. This zymogen has been created by re-designing the enzyme to link the amino and carboxyl termini of the native protein with a loop or bridge of newly designed amino acids. The loop includes in it a target cleavage site for a specific protease. The bridge of novel amino acids extends across the active catalytic site of the ribonuclease, to thus render the ribonuclease incapable of catalytic activity when the inserted amino acids in the bridge are present and intact. However, the provision in the amino acid bridge region for the protease cleavage site permits a specific protease to digest the bridge, and thereby expose the active catalytic site of the enzyme. In the example described here, the protease plasmepsin II was chosen to be the specific protease to cleave a recognition site for this protease built in the amino acids of the bridge region. The protease plasmepsin II is produced by *Plasmodium falciparum*, which is the parasitic organism responsible for most cases of malaria. *Plasmodium falciparum* lives in mature red blood cells which, at maturity, have neither RNA nor DNA metabolism. Thus an active cytotoxic ribonuclease in such a cell would be lethal to the parasite itself, but not to the mature red blood cell. This was intended to be an example of such a protease, with it being contemplated that the use of other proteases is possible.

It was reasoned that an RNase A zymogen could be created by building a bridge of amino acids that extends from the amino terminus to the carboxyl terminus of the mature protein. By studying the three dimensional structure of RNase A, it was observed that a bridge region extending between the termini of the native protein would extend across and interfere with access to the site of ribonucleolytic activity. In order to express a protein having a chain of amino acids linking the amino and carboxyl terminus of the native protein, however, it was necessary to design new ends for the new protein. Thus it was necessary to introduce different loci within the protein for a new amino terminus and new carboxyl terminus. This was done by a process known as circular permutation. A series of DNA constructs were constructed which encoded various permutations of the entire protein, with the bridge region, each permutation having different new carboxyl and amino termini. Various locations were tested within the protein for locating the amino and carboxyl termini of the newly created zymogen. It was also possible, in the design of such a zymogen, to add additional cysteines near the new amino and carboxyl termini so that a disulfide bridge could exist between the newly created termini to help the protein assume the correct three dimensional structure for catalytic activity. In the example described here, a new disulfide bond was introduced into the engineered protein resulting in improved thermal stability.

While the locations of the carboxyl and amino termini of the RNase A protein were particularly convenient for the creation of a bridge of this type to interfere with enzymatic activity, as the three dimensional structure of other proteins are identified, it is expected that this strategy can be adapted for other enzymes. Enzymes that would be appropriate for this approach would be those proteins that have amino and carboxyl termini which, if joined by a bridge region of amino acids, would find their active sites blocked by the bridge.

The work described here was directed first at the enzyme RNase A. The concept of applying the circular permutation technique is illustrated in FIG. 1A. In the native form of the enzyme, in the left-hand image in FIG. 1A, the native protein has normal termini labeled N and C, which are located adjacent to opposite sides of the active site of enzymatic activity. In the middle image in FIG. 1A, the new engineered zymogen, with the new termini N and C, is illustrated with the bridge region extending over, and blocking access to, the enzymatic site. When the zymogen contacts the protease with attacks the protease recognition site in the bridge region, the bridge region in cleaved. This cleavage created the activated form of the enzyme, illustrated in the right-hand image in FIG. 1A.

FIG. 1B and FIG. 1B illustrate two three dimensional images of RNase A zymogens constructed in accordance with this invention. Both show the bridge region, designated "linker" in FIG. 1, bridging across the site of enzymatic activity. These images are intended to illustrate the concept that the bridge region spans the native site of enzyme activity.

Figure 2:
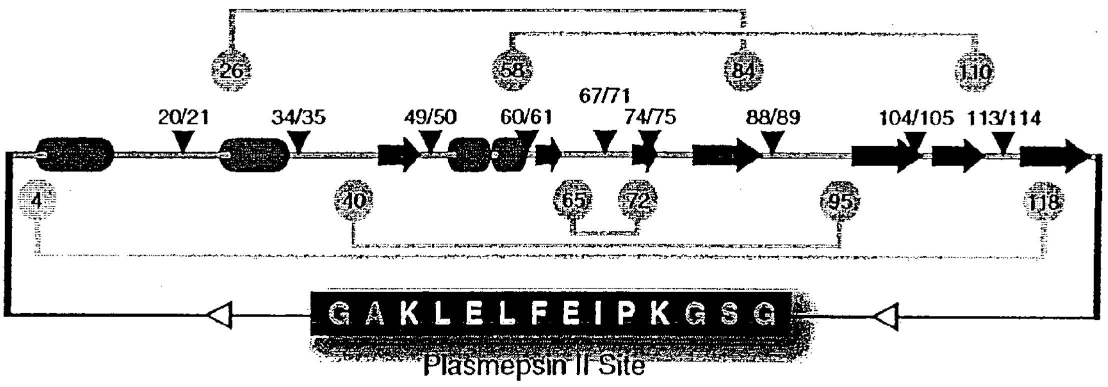
FIG. 2 shows the locations of the disulfide bonds in the RNase A protein.

The native RNase A protein includes four disulfide linkages between cysteine residues. The location of each of the disulfide bonds is illustrated a schematic view of the protein sequence presented in FIG. 2. Note that the inventors here, simply to add stability to the protein by linking the old termini to each other, artificially added the disulfide bond indicated between amino acids 4 and 118. All the other illustrated disulfide bridges are native to the enzyme. The circular permutation strategy was used to create new termini for the protein in each interval between all the natural cysteine residues. The site of each of these termini insertions is indicated in FIG. 2 by the designations 20/21, 34/35, 49/50 etc. This terminology indicates that the new termini were created between the amino acids numbered 20 and 21, or 34 and 35, or 49 and 50 and so on in the native protein. In attempting to find a variation on this zymogen strategy for RNase A that would yield a successful result, the nine potential sites for new termini of the protein were selected as indicated in FIG. 2. Each of the termini sites was located between a unique pair of cysteine residues so that each promuted protein would have a distinct disulfide bonding pattern. In addition, most of the new termini created in this process were located in beta turns or surface loops, which are thought to be more likely to be tolerant of three dimensional change than would an alpha helix or a beta strand.

The maximum distance between corresponding atoms of adjacent residues in a polypeptide chain is about 3.8 Angstroms. The distance between the original amino and carboxyl terminal of the mature RNase A protein is about 30 Angstroms. Thus the distance between the amino and carboxyl terminus could be spanned by a new amino acid bridge containing as few as eight residues. An amino acid linkage connecting the original amino and carboxyl termini must, however, be long enough to leave intact the structure of RNase A and further long enough to allow access by the protease, but short enough to prevent the binding between the enzyme and RNA. By doing molecular modeling, it was reasoned that a linker of fourteen residues would meet these criteria. In the working example below, the fourteen residue bridge region contains the nine residue sequence recognized by plasmepsin 2, a glycine residue at each end to enhance flexibility of the linker, and an additional glycine, alanine, and serine residue. It is preferred for a pancreatic-type ribonuclease that the bridge region is between 12 and 16 residues in length. There should be at least two small flexible amino acids, such as glycine, alanine or serine, located on either side of the protease recognition site, to provide for enough flexibility in the structure of the bridge region for proper interaction with the protease.

The zymogen described in the example below is designed to be activated by the protease plasmepsin II. The demonstration that this protease can be used to activate enzymatic activity teaches that other proteases can also be similarly used. Table 1 below is a table of exemplary organisms or cell types, their unique proteases, and the protease cleavage site for that protease. This table can be used to design zymogens which will be activated when they encounter any specific one of these organisms or cells. The protease should, of course, cleave the bridge region with more activity and rapidity that the bridge region is attacked by any native protease in the human body.

TABLE 1

Zymogen Targets

| Disease | Protease | Cleavage Sequence |
|---|---|---|
| Malaria | plasmepsin II | KPIEF(SEQ ID NO:1)/LELK (SEQ ID NO:2) |
| AIDS | HIV-1 | TATIM(SEQ ID NO:3)/MQRGN (SEQ ID NO:4) |
| Hepatitis C | NS3 | EDVVCC(SEQ ID NO:5)/SMSYK (SEQ ID NO:6) |
| SARS | 3CLp | VSRTLQ(SEQ ID NO:7)/SGFK (SEQ ID NO:8) |
| Ovarian cancer | MMP9 | GPLG(SEQ ID NO:9)/MLSH (SEQ ID NO:1O) |
| Leukemia | HTLV-1 | KGPPVIL(SEQ ID NO:11)/PIQAP (SEQ ID NO:12) |

The successful results here have demonstrated here that it is possible to create a new carboxy and amino terminus of a protein, add a linker of significant size between the amino terminus and carboxyl terminus of the native protein, and still create active enzymatic molecules. It was not known that this could be done before the work described here.

In order to be an effective zymogen, the catalytic activity of the enzyme must be high and must be much greater than any catalytic activity which can be achieved by the unactivated zymogen. In addition, the zymogen must have high conformational stability both before and after activation. In the process described here, we were able to make five RNase zymogens and all five had ribonuclelytic activity which increased after incubation with the protease plasmepsin II. This result suggests that all the zymogens did fold into a structure very similar to the native RNase A, and a structure in which the bridge region interferes with the binding of an RNase substrate to the enzyme. Moreover, the similar ribonucleolytic activity of the unactivated zymogen suggests that each had a similar structure and that the linker provides a similar obstruction in each of these zymogens. By contrast, the large range of ribonucleolytic activity of the zymogens after activation by plasmepsin II suggests that the new amino and carboxy termini of the protein engender different conformations of the enzyme after the bridge region is cleaved. The differences in activity of the zymogens before and after exposure to the protease was significant. Thus it is apparent that some termini will work better than others for zymogen constructed in accordance with the present invention.

The zymogen should thus have much more activity when activated by the protease as compared to the activity before activation. The zymogen created by the 88/89 termini of RNase A, with the plasmepsin II recognition site in the bridge region, had nearly 1000 times greater activity after exposure to the protease. This level of difference is what is desired. It is also desirable that the zymogen have tolerance and activity at and above physiological temperature levels. The 88/89 zymogen molecule, with the inserted disulfide bond between amino acids 4 to 118, had a $T_m$ of over 40° C.

Figure 4:
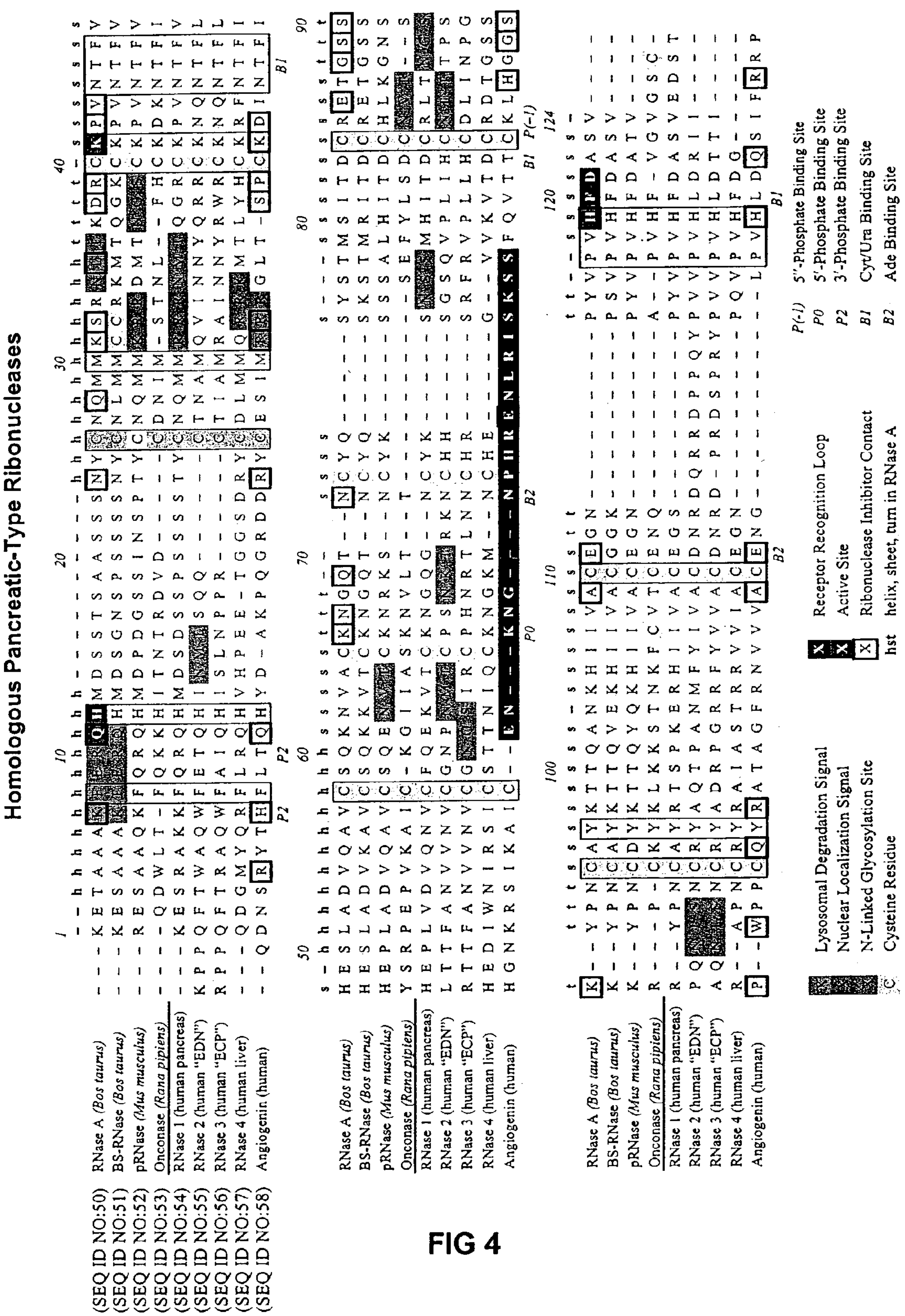
FIG. 4 is a sequence comparison of the amino acid sequences of several pancreatic-type ribonuclease enzymes.

The data presented here demonstrated that the zymogen with the termini located at positions 88 and 89 of the native protein offered the best results. Topological reasoning suggests that any similar insertion of termini between the flanking cysteine residues should have similar results. Referring to FIG. 2, this would permit the termini to be inserted anywhere between amino acids 84 and 95 with similar results. This same locus is present in other highly related pancreatic-type ribonucleases. Shown in FIG. 4 is a listing of nine homologous pancreatic-type ribonucleases, including human ribonucleases such as RNase 1. This alignment of these protein sequences permits the analogous manipulations of these enzymes to that performed with RNase A here. For example, the amino acids glycine 88 and serine 89 of RNase A correspond to the amino acids asparagine 88 and glycine 89 of RNase 1. The region between disulfide bonds, cysteine 84 to cysteine 95 of RNase A, corresponds to the region of cysteines 84 and 95 of RNase 1. Similar analogies can be made to the other enzymes in FIG. 4.

Also, as described below, when an effective zymogen was identified, further engineering of that protein for thermal stability was desired and accomplished. Another artificial disulfide bond between amino acids 4 and 118 was introduced into the zymogen to successfully increase the thermal stability of the enzymatic form of the protein. This disulfide bond was inserted to connect the former termini of the protein, so as to increase the stability of the protein in its three dimensional form. It is desired that such modifications be performed so that the melting temperature, or the temperature at the midpoint of the thermal transition between folded and unfolded states, is at least 10 degrees Centigrade above physiological temperatures.

It is expected that the particular zymogen described here, the RNase A zymogen, will readily be taken up by target cells. Normally RNase A enters cells easily. If the alterations for the zymogen alter the cellular transport of the zymogen RNase A, the zymogen can further be engineered to add a protein translocation domain or a poly-arginine tail to the new C- or N-termini, to accomplish cellular uptake. Many such protein translocation domains effective to mediate cellular uptake are known.

It is, of course, also contemplated that the ribonuclease can be made cytotoxic. The earlier referenced U.S. Pat. No. 5,840,296 and No. 6,280,991 teaches how that may be done. It is possible to make the zymogen as described here, and add new amino acids to the protein to prevent inhibition by ribonuclease inhibitor, as described in that patent.

In general, to construct zymogens according to the present invention, an amino acid bridge is added stretching between the termini of the native protein. New termini are then inserted into the protein. The various circular permutations made are then expressed and tested for activity before and after cleavage. The best performing zymogens are then selected for development. This process should be generally available for other enzymes the three-dimensional structure of which permits this approach.

While this patent specification contains several examples of protein and amino acid sequences, it should be understood that all protein sequences are subject to minor changes and modifications without fundamentally changing the proteins or the concept of the present invention. Conservative changes of amino acids of similar size and polarity are always possible and rarely change the functioning of a protein. The whole zymogen is subject to further modifications of sequence, either by minor amino acid addition, deletion of substitution without adversely affecting the activity as a zymogen. These kinds of changes in amino acid sequence are interpreted to be within the scope of the language used herein.

EXAMPLES

1. Experimental Overview

Design of RNase A Zymogen

Using the logic described above, it was reasoned that an RNase A zymogen could be created by building a bridge of amino acids that would span the active site of RNase A and interfere with the binding of substrate RNA to RNase A. The bridge designed would connect the original N- and C-termini and contain the recognition sequence for a specific protease. New N- and C-termini would be created in the RNase A protein by circular permutation of the polypeptide chain. A critical aspect of this design is that the new N- and C-termini should not be located in a region critical for conformational stability of the protein or ribonucleolytic activity. Otherwise, the zymogen would not fold properly, and no ribonucleolytic activity would be restored after activation. This concept is shown in FIG. 1.

RNase A has eight cysteine residues that form four disulfide bonds in the native enzyme. These disulfide bonds are known to contribute greatly to the conformational stability of the enzyme. The circular permutation of a protein is known to often decrease the conformational stability of the protein. To help ameliorate these concerns, the most stable known variant of RNase A was used as a template for making the zymogens described here. This variant, known as A4C/V118C RNase A, has all four native disulfide bonds plus a normative fifth disulfide bond added between an N- and C-terminal residue, as described in Klink and Raines, *J. Biol. Chem.* 275:17463–17467 (2000). This RNase A is a variant of bovine pancreatic RNase A, which was chosen for this study since it is the most widely characterized RNase A. This enzyme is often used as a model for work on other pancreatic-type ribonucleases.

The process of inserting new termini into a protein, done before to investigate protein folding, involves inserting new termini into what had been the interior of the protein previously. The location of the new termini was thought to be critical to the successful creation of a circular permutation. We selected nine sites for new termini. Each of these nine sites was selected to be between a unique pair of cysteine residues, so that each permuted protein would have a distinct disulfide-bonding pattern. In addition, most of the new termini were in β-turns or surface loops, which are likely to be more tolerant of change than α-helices or β-strands. Attributes of the sites chosen for the new termini are described as follows, with reference to the amino acid numbers in the RNase A into which the new termini were inserted.

20/21. This site was chosen since subtilisin cleaves RNase A between residues number 20 and 21 to produce S-peptide and S-protein. It was previously known that these two protein fragments will associate with each other and totally reconstitute fill ribonucleolytic activity.

34/35 and 49/50. These sites were chosen since they are cleavage sites for other proteases. Thermolysin cleaves RNase A between residues 34 and 35 and 45 and 46, and trypsin cleaves RNase A between residues 31 and 32.

60/61 and 67/71. This site was chosen since residues between Cys58 and Cys72 are relatively unstructured and not conserved in homologues of RNase A. This entire region has been swapped between homologues. Thus there was reason to suspect that modifications to this region would not affect RNase activity.

74/75 and 104/105. Residues 74–75 and 104–105 are in the β-turns of β-hairpins. The β-strands of these hairpins are held together by many hydrogen bonds. It was thought that a cleavage here might permit the protein to still have correct conformational shape.

88/89. Residues 88/89 are in a surface loop. Replacing Gly88 with an arginine residue has little effect on the conformational stability and catalytic activity of RNase A, but greatly disrupts its interaction with ribonuclease inhibitor, as described in Leland et al., *Proc. Natl. Acad. Sci. USA* 95:10407–10412 (1998).

113/114. Swapping of the C-terminal domain near residues 113 and 114 between monomers of RNase A can generate dimers and trimers that maintain ribonucleolytic activity.

G88R. Only those ribonucleases that evade RI are cytotoxic. Hence, all of the variants, except the one with 88/89 termini, had an arginine residue at position 88.

Choice of an Activator Protease

We also had to develop criteria for the candidate protease chosen to activate the zymogen. First, the protease must have a specific cleavage sequence so that non-targeted proteolytic cleavage would be minimal. Otherwise, the protease could damage the enzyme. Second, target cells must be the only cells that contain the protease. Likewise, there should not be any homologue of that specific protease in normal cells.

For the example described here, plasmepsin II was chosen. Plasmepsin II is an aspartic protease that is specific to *Plasmodium falciparum*, the organism responsible for most malaria. Found largely in food vacuoles and also on the cell surface of the parasite, plasmepsin II is itself synthesized as a zymogen. Proplasmepsin II, which has integral membrane type II topology, is processed to become the mature protease starting approximately 12 hours after infection, in the mid-trophozoite stage of the parasitic life cycle. Plasmepsin I, a homologue of plasmepsin II, is also found in the food vacuoles of *Plasmodium falciparum*. Plasmepsin II is more abundant during the intraerythrocytic stage of the parasite life cycle. Both of these enzymes catalyze the cleavage of human hemoglobin and are essential enzymes for the parasite. These proteases are targets for design of new drugs for malarial treatment, as their inhibition has been shown to be lethal to parasites in vitro. The optimal amino acid sequence in the P5-P4' positions of the plasmepsin II cleavage site is KPIEFLELK(SEQ ID NO:13).

Design of Linker

The amino acid bridge for the zymogen must include the protease cleavage site, but the bridge was longer than the cleavage site and additional amino acids were needed. The maximum distance between corresponding atoms of adjacent residues in a polypeptide chain is 3.80 Å. The distance between the original N- and C-termini of native RNase A is approximately 30 Å, a distance that could be spanned by as few as 8 amino acid residues. A bridge connecting the original N-and C-termini must, however, be long enough to leave intact the structure of RNase A and to allow access by plasmepsin II, but short enough to prevent the binding of substrate RNA. Our molecular modeling suggested that a linker of 14 residues with the sequence GSGKPIEFLELK-AG(SEQ ID NO:14) (FIG. 2) would meet these criteria. The linker contained the 9-residue sequence recognized by plasmepsin II, a glycine residue at each end to enhance flexibility, and an additional glycine, alanine, and serine residue. To test whether the length of the bridge was critical, bridges of varying length were designed. The bridge sequences were: GS<u>KPIEFLELK</u>AG(SEQ ID NO:15), GSG <u>KPIEFLELK</u>AG(SEQ ID NO:14), and GSG <u>KPIEFLELK</u>GAG(SEQ ID NO:16) for the loops of 13, 14, and 15 residues, respectively, with the plasmepsin II recognition sequence underlined.

Preparation of RNase A Zymogens

RNase A zymogens were prepared by using an *Escherichia coli* system developed for the production of wild-type RNase A, as described in delCardayre et al. *Protein Eng.* 8:261–273 (1995). In this system, RNase A is isolated initially as an inclusion body, and then subjected to oxidative folding in vitro. Of the nine zymogens designed above, it was found that only five of the nine RNase A zymogens were able to fold properly. These five had termini at 20/21, 67/71, 88/89, 113/114, and 104/105. Fractions of properly folded zymogen were separated from improperly folded zymogen by gel filtration chromatography.

The properly folded protein from gel filtration chromatography was subjected to further purification by cation-exchange chromatography, with elution by a linear gradient of NaCl. The RNase A zymogens eluted at approximately 0.28 M NaCl. The resulting proteins were judged to be in excess of 95% pure based on SDS-PAGE.

Activation of RNase A Zymogens

The properly folded RNase A zymogens were then subjected to electrophoresis in a polyacrylamide gel and screened for ribonucleolytic activity before and after incubation with plasmepsin II. After the incubation, two smaller fragments appeared in each of the gels, and the ribonucleolytic activity increased. The proteolytic cleavage by plasmepsin II was complete within 10 minutes at an approximately 1:100 molar ratio of protease to zymogen. No additional increase in enzyme activity and no other cleavage products were observed after 10 minutes of incubation. Moreover, the cleavage products were stable in the presence of plasmepsin II for at least 2 hours without any further degradation or decrease in ribonucleolytic activity.

The RNase A zymogens with termini at 20/21, 67/71, 88/89, 113/114, and 104/105 were assayed for ribonucleolytic activity before and after activation by plasmepsin II and the results of that assay are presented in Table 2. The values of $k_{cat}/K_M$ for the RNase A zymogens were $10^3$ to $10^4$ $M^{-1}s^{-1}$, which is $10^3$ to $10^4$-fold less than that of wild-type RNase A ($3.6\times10^7$ $M^{-1}s^{-1}$). After activation, RNase A zymogens were able to exhibit ribonucleolytic activity, but the degree of enzymatic activity varied greatly. For example, the zymogen with a 67/71 termini gained only a five-fold increase in activity after cleavage by plasmepsin II, whereas the zymogen with 88/89 termini gained nearly $10^3$-fold increase in activity, and had a $k_{cat}/K_M$ value that was only twofold less than that of wild-type RNase A.

Effect of Disulfide Bonds

The number of disulfide bonds in the RNase A zymogen with 88/89 termini and 14 amino acids linker loop was then subjected to modification to try to increase the thermal stability of the active enzyme. The non-natural disulfide bond between Cys4 and Cys118 was removed by reverse mutation of Cys4 to Ala and Cys118 to Val. This non-natural disulfide bond was the closest bond to the bridge sequence. Hence, the removal of this disulfide bond could decrease any constraint imposed by the bridge and result in an increase in conformational stability. In a separate experiment, a new disulfide bond was introduced between residues number 88 and 89 in this zymogen, an introduced disulfide bond intended to connect the new termini.

The removal of disulfide bond between residues number 4 and 118 had little effect on the conformational stability of the RNase A zymogen. In contrast, the introduction of a new terminal disulfide bond increased the conformational stability greatly, increasing the $T_m$ from 42 to 50° C. before activation and from 48 to 60° C. after activation. Thus this change did add to the thermal stability of the enzyme.

TABLE 2

Values of $k_{cat}/K_M$ ($10^3 M^{-1}s^{-1}$) and $T_m$ (° C.) for ribonuclease A zymogens with various termini before and after activation by plasmepsin

| | 20/21 | 34/35 | 49/50 | 60/61 | 67/71 | 74/75 | 88/89 | 104/105 | 113/114 |
|---|---|---|---|---|---|---|---|---|---|
| ($k_{cat}/K_M$) unactivated | 10.2 | nd | nd | nd | 8.0 | nd | 16.7 | 12.6 | 5.1 |
| ($k_{cat}/K_M$) activated | 496 | nd | nd | nd | 24.0 | nd | 16100 | 1160 | 298 |
| ($k_{cat}/K_M$) activated / ($k_{cat}/K_M$) unactivated | 48.6 | nd | nd | nd | 3.0 | nd | 964 | 92.1 | 58 |
| ($T_m$) unactivated | 48 | nd | nd | nd | 52 | nd | 42 | 42 | 45 |
| ($T_m$) activated | 52 | nd | nd | nd | 58 | nd | 48 | 51 | 53 |

nd, not determined

Conformational Stability of RNase A Zymogens

The folded RNase A zymogens were assayed for conformational stability both before and after activation by plasmepsin II, as shown in Table 2 above. All of the RNase A zymogens had a $T_m$ value in PBS that was greater than 37° C. but lower that of wild-type RNase A (62° C.). The value of $T_m$ for the unactivated RNase A zymogens ranged from 42 to 52° C. Activation by plasmepsin II increased the value of $T_m$ by 5 to 9° C.

Effect of Bridge Size

The ideal zymogen should have low activity before activation, but would have high activity after activation. Of the above zymogens, the RNase A zymogens that best met this criteria had 20/21 and 88/89 termini. The zymogen with 88/89 termini had a large increase in activity after activation, but a low $T_m$ value before plasmepsin II activation. The zymogen with 20/21 termini had a high $T_m$ value and a modest increase in activity after activation. These two variants were then subjected to further modifications.

The length of the bridge was varied from 13 to 15 residues, using the amino acid sequences described above. There was no significant change in either the conformational stability or the ribonucleolytic activity of these RNase A zymogens variants, except for that with 88/89 termini and a 15-residue linker. That variant exhibited a significantly higher ribonucleolytic activity before plasmepsin II activation. Hence, a linker of 13 or 14 residues was deemed to be sufficient.

2. Detailed Methods and Materials

Materials

*Escherichia coli* strains BL21(DE3) and BL21(DE3) pLysS were from Novagen (Madison, Wis.). *E. coli* strain DH-5α was from Life Technologies. A plasmid encoding A4C/G88R/V118C RNase A was described previously. All restriction endonucleases were from Promega (Madison, Wis.) or New England Biolabs (Beverly, Mass.). Pfu DNA polymerase was from Stratagene (La Jolla, Calif.). Taq DNA polymerase and RI were from Promega. A plasmid encoding plasmepsin II was a generous gift of B. M. Dunn (University of Florida, Gainesville, Fla.).

Purified oligonucleotides and the fluorogenic substrate 6-carboxyfluorescein-dArU(dA)$_2$-6-TAMRA (6-FAM-dArU(dA)$_2$-6-TAMRA) were from Integrated DNA Technologies (Coralville, Iowa). DNA sequences were determined with a Big Dye kit, FS from Perkin-Elmer (Foster City, Calif.), PTC-100 programmable thermal controller from MJ Research (Watertown, Mass.), and 373XL automated sequencer from Applied Biostystems (Foster City, Calif.) at the University of Wisconsin Biotechnology Center.

Terrific broth medium contained (in 1 liter) Bacto tryptone (12 g), Bacto yeast extract (24 g), glycerol (4 ml), $KH_2PO_4$ (2.31 g), and $K_2HPO_4$ (12.54). It was prepared in distilled water and autoclaved. M9 minimal medium contained (in 1 liter) $Na_2HPO_4.7H_2O$ (12.8 g), $KH_2PO_4$ (3.0 g), NaCl (12.8 g), $NH_4Cl$ (12.8 g), $MgSO_4$ (0.5 g), and $CaCl_2$ (0.5 g). PBS contained (in 1 liter) KCl (0.20 g), $KH_2PO_4$ (0.20 g), NaCl (8.0 g), and $Na_2HPO_4.7H_2O$ (2.16 g).

Instrumentation

UV absorbance measurements were made on a Cary Model 3 or 50 spectrophotometer from Varian (Palo Alto, Calif.) equipped with a Cary temperature controller. Fluorescence measurements were made on a QuantaMaster1 photon-counting fluorometer from Photon Technology International (South Brunswick, N.J.) equipped with sample stirring. Molecular modeling and energy minimization was done with the program SYBYL from Tripos (St. Louis, Mo.) on an Octane computer from Silicon Graphics (Mountain View, Calif.).

Construction of a Plasmid to Produce RNase A Zymogens

Figure 3:
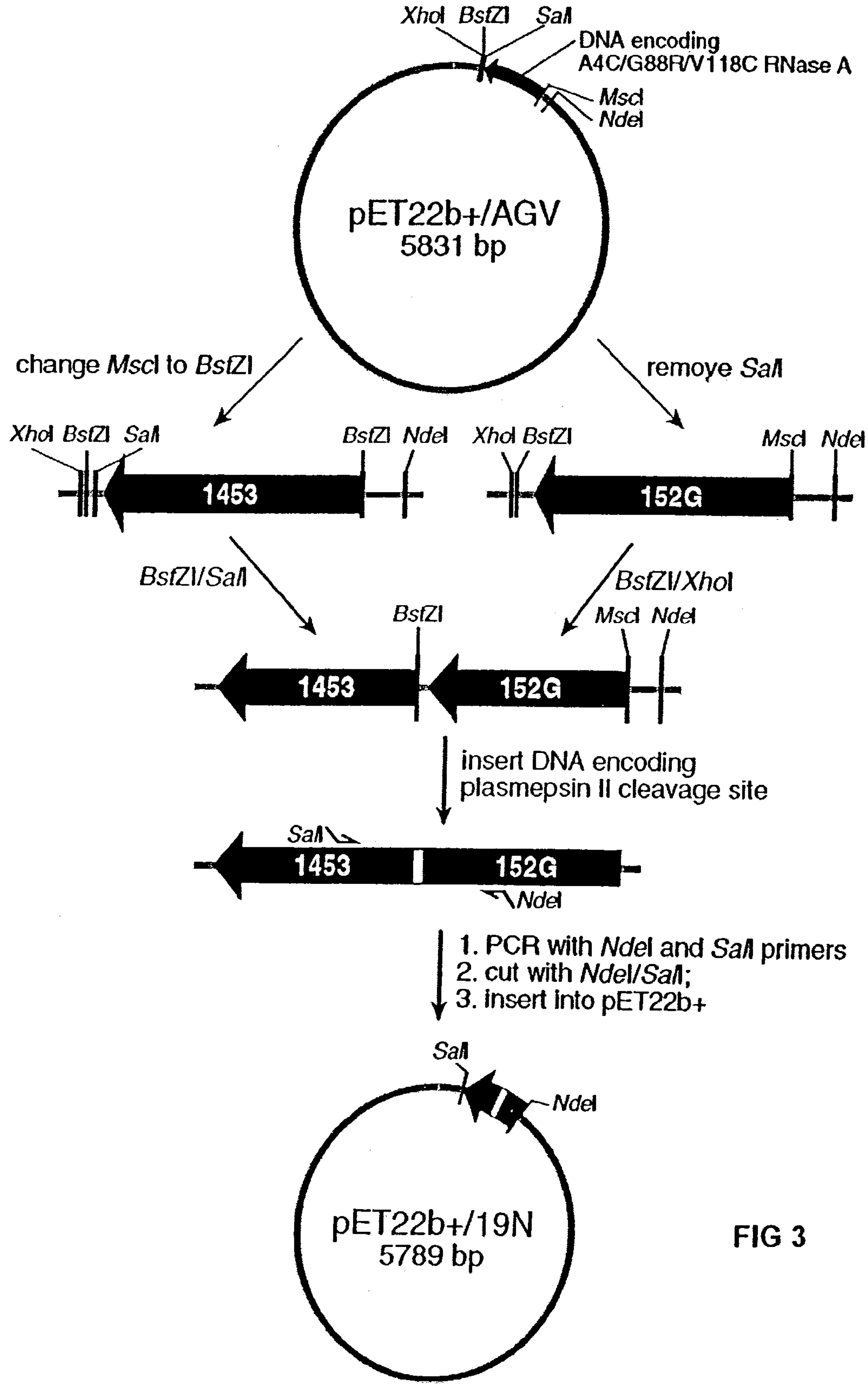
FIG. 3 shows the steps in construction of a plasmid to express the zymogen of the examples below.

A scheme showing the construction of a plasmid pET22b+/19N, which directs the expression of an RNase A zymogen, is shown in FIG. 3. Plasmid pET22b+/AGV, which directs the expression of A4C/G88R/V118C RNase A, served as the starting material. The MscI site was replaced with a BstZI site by single-stranded DNA mutagenesis using the oligonucleotide 5'CAC AAG TTT CCT TGC CGG CCG CCG GCT GGG CAG CGA G 3' (SEQ ID NO:17), resulting in a plasmid designated p1453. The SalI site was removed by using the oligonucleotide 5' CCG CAA GCT TGT CGA GGA TCC CAC TGA AGC ATC AAA 3' (SEQ ID NO:18), resulting in a plasmid designated p152G. Plasmid p1453 was subjected to digestion with BstZI and SalI endonucleases, and a 385-bp fragment was purified after electrophoresis in an agarose gel. Plasmid p152G was subjected to restriction enzyme digestion with BstZI and XhoI endonucleases, and a 5805-pb fragment was purified. The two DNA fragments were ligated (XhoI and SalI digestion yield compatible cohesive ends), resulting in a plasmid pSMFII. Plasmid pSMFII was then subjected to digestion with BamHI and BstZI endonucleases, and a 6190-fragment was purified. A phosphorylated double-stranded oligonucleotide encoding a plasmepsin II cleavage sequence within 13, 14, or 15 amino acid residues and having BstZI and BamHI compatible cohesive ends was ligated to the pSMFII/BstZI/BamHI fragment (5' GAT CTA AAC CGA TTG AAT TTC TGG AAC TGA A 3' (SEQ ID NO:19) and 5' GGC CTT CAG TTC CAG AAA TTC AAT CGG TTT A 3' (SEQ ID NO:20) for the 13-residue linker, 5' GAT CTG GCA AAC CGA TTG AAT TTC TGG AAC TGA A 3' (SEQ ID NO:21) and 5' GGC CTT CAG TTC CAG AAA TTC AAT CGG TTT GCC A 3' (SEQ ID NO:22) for the 14-residue linker, and 5' GAT CTG GCA AAC CGA TTG AAT TTC TGG AAC TGG GCA A 3' (SEQ ID NO:23) and 5' GGC CTT GCC CAG TTC CAG AAA TTC AAT CGG TTT GCC A 3' (SEQ ID NO:24) for the 15-residue linker). Oligonucleotide primers corresponding to different new N-termini were engineered to have an NdeI-compatible cohesive end, and those corresponding to different new C-termini were engineered to have a SalI-compatible cohesive ends, as shown in Table 3. These pairs of primers were used in the PCR, and the resulting products were purified and subjected to digestion with NdeI and SalI endonucleases. The resulting fragments were inserted into NdeI and SalI sites of plasmid pET22b+, to produce plasmid pET22b+/19N.

The disulfide bond between Cys4 and Cys118 was removed from the circular permuted RNase A with 88/89 termini by PCR-based site-directed mutagenesis using oligonucleotides 5' AAG GAA ACT GCA GCA GCC AAG TTT GAG CGG CAG C 3' (SEQ ID NO:25) and 5' GCT GCC GCT CAA ACT TGG CTG CTG CAG TTT CCT T 3' (SEQ ID NO:26) to replace Cys4 with an alanine residue and 5' GCA TCA AAG TGG ACT GGC ACG TAC GGG TTT CCC 3' (SEQ ID NO:27) and 5' GGG AAA CCC GTA CGT GCC AGT CCA CTT TGA TGC 3' (SEQ ID NO:28) to replace Cys118 with a valine residue. The C4A replacement was screened by digestion with PstI endonuclease, and the C118V replacement was screened by digestion with BsiWI endonuclease.

The permuted RNase A with an 88/89 termini and sixth disulfide bond was created by PCR of plasmid pSMFII using oligonucleotide primers 5' CGT GAG CAT ATG TGT TCC AAG TAC CCC 3' (SEQ ID NO:29) and 5' GTT GGG GTC GAC CTA CTA GCA CGT CTC ACG GCA GTC 3' (SEQ ID NO:30) with NdeI and SalI restriction sites. The PCR product was purified, digested with NdeI and SalI endonucleases, and inserted into complementary pET22b+. The resulting plasmid encodes a permuted variant with the eight native cysteine residues plus Cys4, Cys88, Cys89, and Cys118.

Oligonucleotides were annealed by dissolving them to 0.25 mM in 10 mM Tris-HCl buffer (pH 8.0) containing NaCl (50 mM) and EDTA (1 mM). The resulting solution was heated to 95° C. in a water bath and cooled slowly (over 4 h) to room temperature. The resulting double-stranded oligonucleotides were subjected to 5'-phosphorylation by treatment for 1 hour with T4 polynucleotide kinase.

TABLE 3

Oligonucleotides Used to Create Ribonuclease A Zymogens

| Start/Stop Residues | Oligonucleotide (5'→3') | |
|---|---|---|
| 20/21 | GTTGACCCGCATATGAGCAGCTCCAACTACTGTAACCAGATGATG | (SEQ ID NO:31) |
| | CGATAAGGC*GTCGA***CTACTA**GGCAGCGGAAGTGCT | (SEQ ID NO:32) |
| 34/35 | GGCCATATGCTGACCAAAGATCGATGCAAG | (SEQ ID NO:33) |
| | CAC*GTCGAC***CTACTA**GTTCCGGCTCTTCATCATC | (SEQ ID NO:34) |
| 49/50 | GGCCATATGTCCCTGGCTGATGTCCAGGCC | (SEQ ID NO:35) |
| | CAC*GTCGAC***CTACTA**CTCGTGCACAAAGGTGTTC | (SEQ ID NO:36) |
| 60/61 | GGCCATATGAAAAATGTTGCCTGCAAG | (SEQ ID NO:37) |
| | CAC*GTCGAC***CTACTA**CTGGGAGCACACGGCCTG | (SEQ ID NO:38) |
| 67/71 | GGCCATATGAATTGCTACCAGAGCTACTCC | (SEQ ID NO:39) |
| | GTG*CTCGAG***CTACTAA**TTCTTGCAGGCAACATT | (SEQ ID NO:40) |
| 74/75 | GGCCATATGTCCACCATGAGCATCACCGAC | (SEQ ID NO:41) |
| | CAC*GTCGAC***CTACTA**GTAGCTCTGGTAGCAATTG | (SEQ ID NO:42) |

TABLE 3-continued

Oligonucleotides Used to Create Ribonuclease A Zymogens

| Start/Stop Residues | Oligonucleotide (5'→3') | |
|---|---|---|
| 88/89 | CAACGCCTTCATATGAGCTCCAAGTACCCCAACTGTGCCTACAAGAC | (SEQ ID NO:43) |
| | CTGACGGC*AGTCGA***CTACTA**CCCTGTCTCACGGCAGTC | (SEQ ID NO:44) |
| 104/105 | GGCCATATGCACATCATTGTGGCTTGTGAG | (SEQ ID NO:45) |
| | CAC*GTCGAC***CTACTA**TTTATTCGCCTGGGTGGTC | (SEQ ID NO:46) |
| 113/114 | GGCCATATGTACGTGCCATGTCACTTTG | (SEQ ID NO:47) |
| | CAC*GTCGAC***CTACTA**GTTTCCCTCACAAGCCAC | (SEQ ID NO:48) |

NdeI restriction sites are underlined, SalI restrictions site are in italics, and stop codon (reverse compliment) are in bold.

5' CGT GAG CAT ATG TGT TCC AAG TAC CCC 3' (SEQ ID NO:29) and 5' GTT GGG GTC GAC CTA CTA GCA CGT CTC ACG GCA GTC 3' (SEQ ID NO:30) with NdeI (bold) and SalI (italics) restrictions sites.

Preparation of RNase A Zymogens

The production, folding, and purification of RNase A zymogen were done as described previously for other variants of RNase A (as in Leland et al., *Proc. Natl. Acad. Sci. U.S.A.* 95:10407–10412 (1998)) except that the oxidative folding was done at pH 7.8 for at least 48 hours.

Preparation of Proplasmepsin II

The production, folding, and purification of proplasmepsin II were done as described previously. Proplasmepsin II was activated by the addition of 1 μl of 1.0 M sodium citrate buffer (pH 4.7) to 9 μl of a solution of proplasmepsin II (10 μM in 20 mM Tris-HCl buffer, pH 8.0) and incubation of the resulting solution at 37° C. for 45 min.

Activation of RNase A Zymogens

RNase A zymogens were activated by mixing 19.5 μl of a solution of zymogen (25 μM) with 0.5 μl of a solution of activated plasmepsin 11 (10 μM), and incubating the resulting mixture at 37° C. for 15 min. Activation was stopped by the addition of pepstatin A to a final concentration of 1 μM. To assess zymogen activation, reaction mixtures were subjected to electrophoresis in a 15% (w/v) polyacrylamide gel containing sodium dodecyl sulfate (SDS; 1% w/v), and assayed for ribonucleolytic activity.

Ribonucleolytic Activity of RNase A Zymogens

The ribonucleolytic activity of RNase A zymogens was evaluated before and after activation with an assay based on a fluorogenic substrate. Cleavage of 6-FAM-dArU$(dA)_2$-6-TAMRA results in a ~200-fold increase in fluorescence intensity (excitation at 492 nm; emission at 515 nm). Assays were performed at 23° C. in 2.0 mL of 0.10 M MES-NaOH buffer (pH 6.0) containing NaCl (0.10 M), 6-FAM-dArU$(dA)_2$-6-TAMRA (50 nM), and zymogen. Data were fitted to the equation: $k_{cat}/K_M=(\Delta I/\Delta t)/\{(I_f-I_0)[E]\}$ where $\Delta I/\Delta t$ is the initial velocity of the reaction, $I_0$ is the fluorescence intensity prior to the addition of enzyme, $I_f$ is the fluorescence intensity after complete hydrolysis with excess wild-type enzyme, and [E] is the ribonuclease concentration.

Conformational Stability of RNase A Zymogens

The conformational stability of RNase A zymogens was assessed before and after activation by recording the change in absorbance at 287 nm with increasing temperature. The temperature of a solution of RNase A zymogen (0.15–0.25 mg/mL) in PBS was increased continuously from 20 to 70° C. at 0.15° C./min. The absorbance was recorded at 1° C. intervals and fitted to a two-state model for denaturation. The temperature at the midpoint of the transition is defined as $t_m$.

We claim:

1. An RNase A zymogen having a bridge of amino acids blocking access to its catalytic site, the bridge having a protease cleavage site within it, the bridge constituted such that conversion of the zymogen to an active enzyme occurs when the zymogen is acted upon by the specific protease.

2. An engineered zymogen of a pancreatic-type ribonuclease, the amino acid sequence of the zymogen varied from the amino acid sequence of the ribonuclease by changes which comprise (a) the addition of a bridge region extending from the native carboxyl terminus of the ribonuclease to the native amino terminus of the ribonuclease, the bridge region having an amino acid sequence having a protease recognition site, and (b) the introduction of a new carboxyl terminus and a new amino terminus in the zymogen, the zymogen being activated by protease which cleaves the protease recognition site which causes the zymogen to then become catalytically active for ribonuclease activity.

3. An engineered zymogen as claimed in claim 2 wherein the changes further comprise the introduction of two new cysteine amino acids in the zymogen located near the new carboxyl and amino termini of the zymogen to assist in the thermal stability of the protein.

4. An engineered zymogen as claimed in claim 2 wherein the ribonuclease is bovine ribonuclease A.

5. An engineered zymogen as claimed in claim 2 wherein the protease recognition site is a cleavage site for the protease plasmepsin 2.

6. An engineered zymogen as claimed in claim 5 wherein the protease recognition site has the sequence GSGKPIEF-LELKAG (SEQ ID NO:14 ).

7. An engineered zymogen as claimed in claim 2 wherein the new carboxyl and amino termini are located in the zymogen in the region of the protein corresponding to the region between amino acids 84 and 95 in bovine ribonuclease A.

8. An engineered zymogen as claimed in claim 7 wherein the new carboxyl and amino termini are located between amino acids corresponding to amino acids 88 and 89 in bovine ribonuclease A.

9. An engineered zymogen as claimed in claim 2 comprising a further change such that the ribonuclease is rendered cytotoxic when activated by the protease.

10. An engineered zymogen as claimed in claim 2 comprising a further change which is that a protein translocation domain is attached to the zymogen.

11. A pancreatic-type ribonuclease zymogen having a bridge of amino acids blocking access to its catalytic site, the bridge having a protease cleavage site within it, so conversion of the zymogen to an active ribonuclease enzyme occurs when the zymogen is acted upon by the specific protease, the active ribonuclease enzyme being cytotoxic when activated by the protease.

12. A method of designing a zymogen of an enzyme comprising the steps of designing a bridge of amino acids which would extend from the carboxyl terminus to the amino terminus of the enzyme, the bridge incorporating a protease cleavage site for a specific protease;

selecting several sites within the enzyme at which new carboxyl and amino termini might be located;

making expression plasmids which will express the zymogens including the bridge and the new termini;

expressing the plasmids in a host and recovering the zymogens expressed; and testing the zymogens for activity before and after exposure to the specific protease to identify zymogens which increase in enzymatic activity after protease cleavage as compared to before the cleavage.

13. A method as claimed in claim 12 in which the enzyme is a pancreatic-type ribonuclease.

14. A method as claimed in claim 13 wherein the specific protease is produced by a human pathogen.

15. A method as claimed in claim 13 wherein the specific protease is produced by human cells in a specific disease state.

16. A method as claimed in claim 12 wherein the method further comprises testing the zymogens for thermal stability to identify a zymogen which would be active at physiological temperatures.

* * * * *

UNITED STATES PATENT AND TRADEMARK OFFICE

CERTIFICATE OF CORRECTION

PATENT NO. : 7,098,016 B2 Page 1 of 1
APPLICATION NO. : 10/461713
DATED : August 29, 2006
INVENTOR(S) : Ronald T. Raines, Parit Plainkum and Stephen M. Fuchs It is certified that error appears in the above-identified patent and that said Letters Patent is hereby corrected as shown below:

In the Specification:

Please delete paragraph "0002" under the heading "STATEMENT REGARDING FEDERALLY SPONSORED RESEARCH OR DEVELOPMENT," Col. 1, and insert therefor the following:

--This invention was made with United States government support awarded by the following agency:

NIH CA 73808

The United States has certain rights in this invention.--

Signed and Sealed this

Thirteenth Day of February, 2007

JON W. DUDAS
*Director of the United States Patent and Trademark Office*